United States Patent
Wampler

(10) Patent No.: US 6,257,241 B1
(45) Date of Patent: *Jul. 10, 2001

(54) METHOD FOR REPAIRING TISSUE DEFECTS USING ULTRASONIC RADIO FREQUENCY ENERGY

(75) Inventor: Scott D. Wampler, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/283,819

(22) Filed: Mar. 31, 1999

(51) Int. Cl.[7] ................................................. A61B 19/00
(52) U.S. Cl. ........................................... 128/898; 623/66.1
(58) Field of Search ............................. 623/66.1; 128/898

(56) References Cited

U.S. PATENT DOCUMENTS

| | | | |
|---|---|---|---|
| 3,272,204 | 9/1966 | Artandi et al. | 128/334 |
| 3,376,869 | 4/1968 | Borysko | 128/334 |
| 3,563,228 | 2/1971 | Seiderman | 128/1 |
| 4,452,245 | 6/1984 | Usher | 128/334 R |
| 4,931,047 | * 6/1990 | Broadwin et al. | 604/22 |
| 5,015,227 | 5/1991 | Broadwin et al. | 604/22 |
| 5,209,776 | 5/1993 | Bass et al. | 106/124 |
| 5,246,156 | 9/1993 | Rothfuss et al. | 227/176 |
| 5,258,000 | 11/1993 | Gianturco | 606/151 |
| 5,470,010 | 11/1995 | Rothfuss et al. | 227/177 |
| 5,733,337 | 3/1998 | Carr, Jr. et al. | 623/11 |
| 5,749,895 | * 5/1998 | Sawyer et al. | 606/214 |
| 5,824,015 | 10/1998 | Sawyer | 606/214 |
| 5,873,873 | * 2/1999 | Smith et al. | 606/1 |
| 5,925,078 | * 7/1999 | Anderson | 623/66 |
| 5,972,007 | * 10/1999 | Sheffield et al. | 606/151 |

FOREIGN PATENT DOCUMENTS

| | | | |
|---|---|---|---|
| WO 92/21300 | 10/1992 | (WO) | A61B/17/39 |
| WO 96/03925 | 2/1996 | (WO) | A61B/17/06 |

OTHER PUBLICATIONS

U.S. application No. 09/282,601, Wampler, filed Mar. 1999.*

* cited by examiner

*Primary Examiner*—Corrine McDermott
*Assistant Examiner*—Thomas Barrett
(74) *Attorney, Agent, or Firm*—Louis J. Capezzuto

(57) ABSTRACT

A method of repairing a defect in tissue includes the steps of placing a prosthetic over a tissue defect and against surrounding tissue. The prosthetic is then embedded into the surrounding tissue by an application of pressure and ultrasonic energy to the prosthetic and the surrounding tissue on at least one location on the prosthetic and surrounding tissue. The embedded prosthetic is then welded into surrounding tissue by an application of pressure and Radio Frequency energy on the same location.

11 Claims, 12 Drawing Sheets

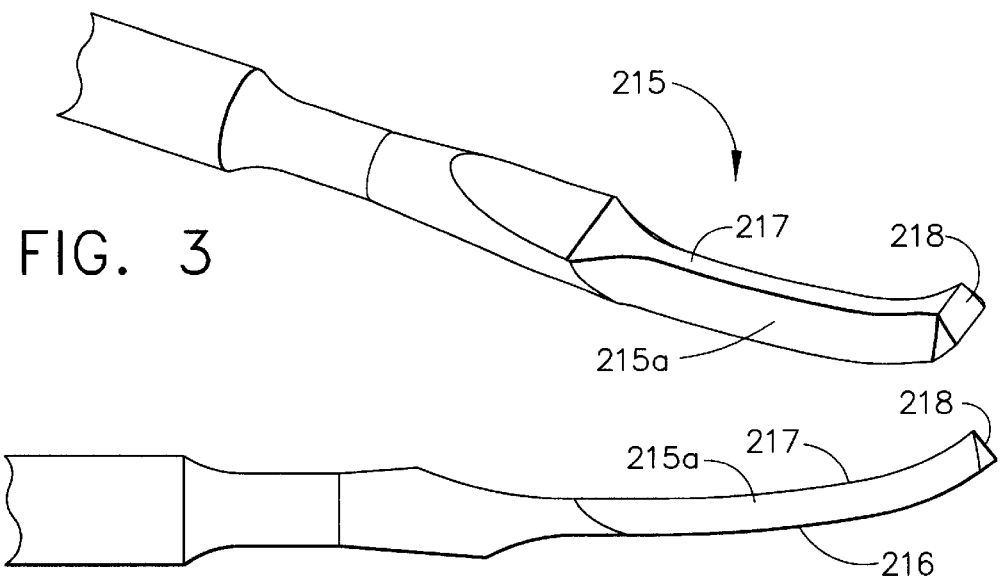
FIG. 3
FIG. 4
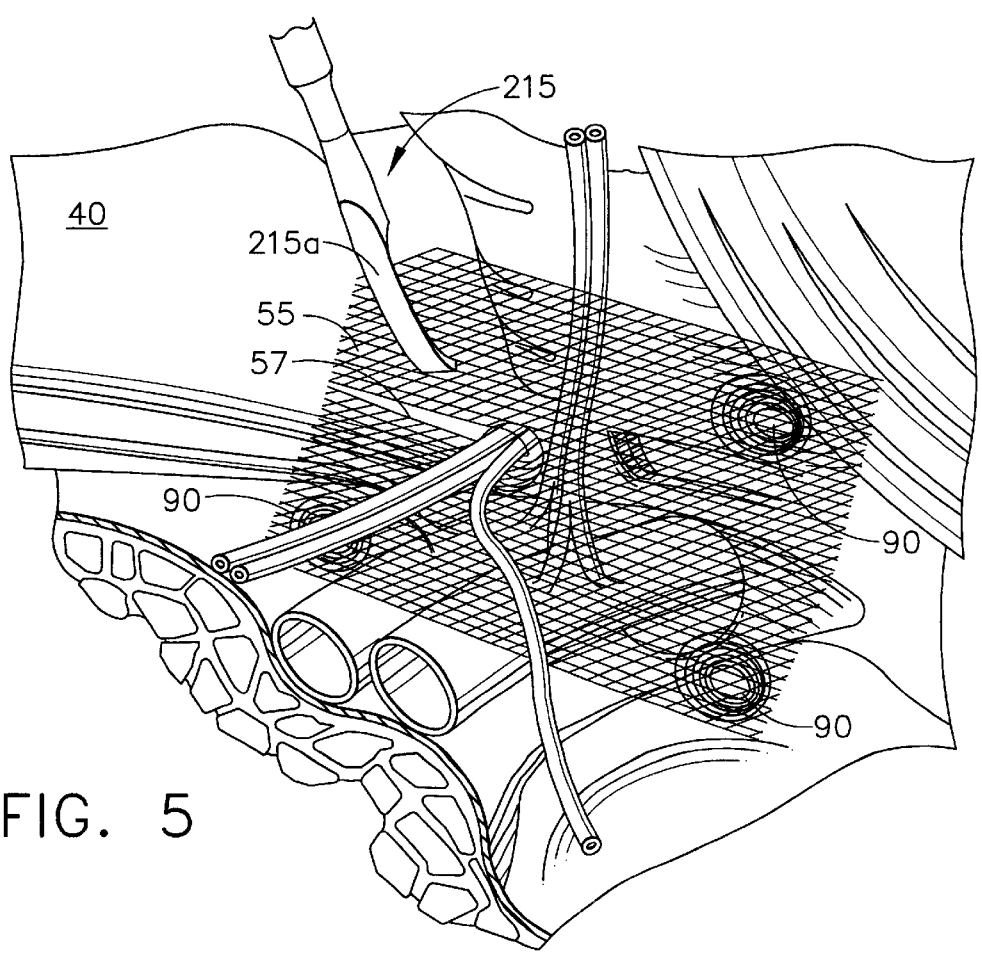
FIG. 5

METHOD FOR REPAIRING TISSUE DEFECTS USING ULTRASONIC RADIO FREQUENCY ENERGY

FIELD OF THE INVENTION

The present invention relates, in general, to the surgical repair of tissue, and more particularly, to a new and useful method for repairing a defect in tissue such as an inguinal hernia utilizing a prosthetic and the application of ultrasonic and Radio Frequency energy.

BACKGROUND OF THE INVENTION

It is established practice in the surgical field to repair defects in tissue, for instance, an inguinal hernia, through the use of PROLENE™ mesh (manufactured and sold by Ethicon, Inc., Somerville, N.J.). Generally the mesh is cut to a desired size for placement over the inguinal hernia. Once the sized mesh has been placed over the defect, the mesh is attached to the surrounding inguinal tissue using several known attachment means.

Once the mesh is in place, it is important that the mesh serve as a barrier over the defect in order to restrict the lower viscera in the patient's abdomen from protruding through the defect. Accordingly, it is essential that the attachment means used to secure the mesh to the inguinal tissue have an initial strength of several pounds of force in both the tensile and shear directions. Moreover, it is important that the mesh remain in place for several days so that natural adhesions can form to ensure that the mesh is sufficiently anchored to the tissue.

One common way of attaching the mesh to tissue is through the use of suture and needle. As would be expected, the suturing technique for this procedure requires a great deal of skill and is normally conducted by very experienced surgeons, especially for minimally invasive or laparoscopic procedures. Since the learning curve for laparoscopic suturing is extremely steep, many surgeons are slow to adopt this technique.

In response to the challenges associated with suturing, other fastening techniques have evolved. Accordingly, it is now common practice to use a surgical stapler such as the ENDOSCOPIC MULTI-FIRE STAPLER™, (manufactured and sold by Ethicon Endo-Surgery, Inc., Cincinnati, Ohio). U.S. Pat. No. 5,470,010 (Rothfuss et al.) discloses a disposable, endoscopic stapler that is used to place a number of staples at various locations of the placed mesh in order to properly secure the mesh to the tissue. Although the endoscopic stapler is efficient and easy to use for a surgeon, there is a cost issue associated with its use for this type of procedure.

In an effort to alleviate the costs associated with a disposable, multiple fire stapler, some surgeons prefer a re-usable, "single shot" stapler such as disclosed in U.S. Pat. No. 5,246,156 (Rothfuss et al.). Although there is a cost savings to the user, the procedure time is extended when using this type of stapler over the disposable, multiple fire stapler.

In addition to using surgical staplers to secure mesh to inguinal tissue to repair a hernia, other types of fasteners have been developed. One of these fasteners is a helical fastener such as disclosed in U.S. Pat. No. 5,258,000 (Gianturco). This type of fastener is also disclosed in WO 96/03925 (Bolduc et al.). However, although these types of fasteners are also easy to use and decrease the procedure time, cost is also an issue.

It is important to note that, presently, the known devices or attachment means for repairing tissue defects are mechanical devices such as endoscopic staplers or fasteners or simple needle and suture. Presently, there are no known energy-based delivery devices or energy-based methods that are capable of performing tissue repair such as that described above.

SUMMARY OF THE INVENTION

The present invention is a novel method for repairing a defect in tissue.

The method, according to the present invention, comprises the steps described below.

A prosthetic is initially provided for placement over a tissue defect and against surrounding tissue. The prosthetic is embedded into surrounding tissue by a first application of pressure and ultrasonic energy to the prosthetic and the surrounding tissue. The pressure and energy are applied on at least one location on the prosthetic and the surrounding tissue. The embedded prosthetic is welded into surrounding tissue by a second application of pressure and Radio Frequency energy on the same at least one location on the prosthetic and the surrounding tissue.

Significantly, the method of this invention provides the surgeon with an improved method of attaching a prosthetic over a tissue defect. This is accomplished by an initial application of ultrasonic energy to the prosthetic and surrounding tissue to embed the prosthetic, and a second application of Radio Frequency energy to weld the prosthetic in place. Consequently, the surgeon is provided with a time saving method of attaching a prosthetic onto tissue. In particular, if the tissue repair is the attachment of a patch over a tissue defect, such as an inguinal hernia, the time-saving can be significant. A preferred prosthetic of the present invention is a mesh patch.

It is an object of the present invention to use ultrasonic energy for the first step of embedding the prosthetic into the surrounding tissue. The application of ultrasonic energy emulsifies the tissue directly beneath the prosthetic and the application of pressure embeds the prosthetic into the emulsified tissue.

It is another object of the present invention to use Radio Frequency energy for the second step of coagulating the emulsified tissue. The second application of Radio Frequency energy is applied to the initial site wherein the prosthetic is embedded in emulsified tissue. This second application of energy coagulates the emulsified tissue around the embedded prosthetic and welds the prosthetic to the surrounding tissue. To appropriately secure the prosthetic over the tissue defect, additional welds may be applied at each of several locations.

It is yet another object to provide another embodiment of the method of the present invention as described below.

The first step is providing an energy based surgical device having a housing, and an acoustic assembly for the generation of ultrasonic energy. The acoustic assembly includes an electrically conductive waveguide that extends from the housing. The waveguide has a solid core. A conductive element is operably coupled to the waveguide for conducting Radio Frequency energy to the waveguide. An end effector is located at the distal end of the acoustic assembly, the end effector having an embedding surface and a coagulating surface.

Next, a prosthetic is placed over a tissue defect and against surrounding tissue. The prosthetic is embedded into surrounding tissue with a first application of ultrasonic energy from the embedding surface of the end effector. An application of Radio Frequency energy is applied to the embedded prosthetic and surrounding tissue by the coagulating surface of the end effector. The Radio Frequency energy is applied at a different energy intensity to weld the embedded prosthetic to the surrounding tissue.

Thus, this embodiment provides the surgeon with a novel energy based surgical device having an embedding surface and a cauterizing surface, and a method of using these surfaces to embed and weld the prosthetic to tissue.

Another object of the invention is to provide a switch mounted upon the housing for the selection of the type of energy deliverable to the end effector. This provides the surgeon with the advantage to easily select, prior to the step of embedding or welding, the type of energy best suited for the application site. The switch provides the selection of ultrasonic, Radio Frequency or a combination of ultrasonic and RF energy.

Three embodiments of the end effector of the energy based surgical device, according to the present invention, are disclosed. A first embodiment of an end effector according to the present invention comprises a truncated cone end effector having an embedding surface at the distal tip. A circumferential coagulating surface is located about the truncated cone and is angled away from the embedding surface.

A second embodiment according to the present invention is a curved end effector having a curved member and at least one distal embedding surface. A coagulation surface extends along the curve of the curved member. Preferably, the coagulation surface is upon the outer curve of the curved member.

A third embodiment of the end effector according to the present invention comprises an angled surface end effector having a cylindrical shaft. An embedding surface is located at the distal end of the cylindrical shaft and an angled coagulating surface extends distally from the embedding surface. The angled embedding surface is angled from a longitudinal axis of the cylindrical shaft and outwardly from the embedding surface.

With respect to all three embodiments of the prosthetic according to the method of the present invention, the surgeon is provided with three end effectors having an embedding surface for emulsifing tissue and a coagulating surface for coagulating tissue as described in the method steps above.

It is an object of the present invention to provide a method for repairing a defect in tissue that is minimally invasive, time and cost effective and easy to use.

It is another object of the present invention to provide a method for repairing an inguinal hernia that is minimally invasive, time and cost effective and easy to use.

The various features of novelty which characterize the invention are pointed out with particularity in the claims annexed to and forming a part of the disclosure. For a better understanding of the invention, its operating advantages and specific objects attained by its uses, reference is made to the accompanying drawings and descriptive matter in which the preferred embodiments of the invention are illustrated.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 3 is a fragmentary perspective view of a curved end effector, according to the present invention;

FIG. 4 is a fragmentary side view of the curved end effector of FIG. 3;

FIG. 5 is a fragmentary perspective view of the initial step of embedding the prosthetic into the inguinal floor with the curved end effector of FIG. 3 just prior to the application of energy according to the present invention;

DETAILED DESCRIPTION OF THE PREFERRED EMBODIMENTS

The present invention pertains to the repair of defects in tissue and includes a novel surgical method for repairing tissue defects using a prosthetic as well as a novel energy based surgical device. More particularly, the invention concerns the use of an improved Radio Frequency energy and ultrasonic energy based surgical device in combination with the prosthetic for the repair of an inguinal hernia.

By way of example, the present invention is illustrated and described in conjunction with a repair of an inguinal hernia. However, it should be understood that the present invention is applicable to various other surgical procedures that require the repair of defects in tissue.

The Anatomy

Figure 1A:
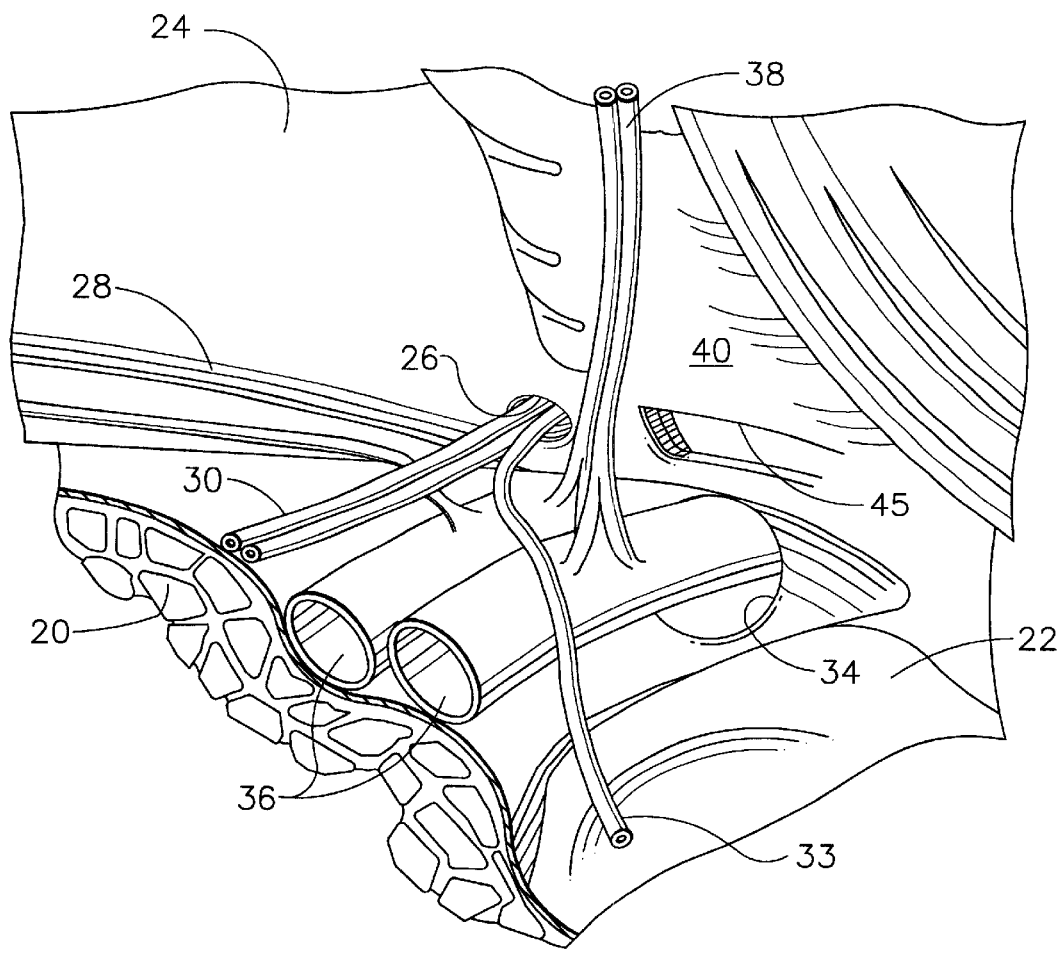
FIG. 1A is a fragmentary perspective view of a defect in the inguinal floor of the lower abdomen, particularly the left inguinal anatomy.

Referring now to FIG. 1A, one typical application of the present invention is a repair of a defect 45, such as an inguinal hernia, located in inguinal tissue 40 such as the inguinal floor. The delicate anatomical structures of the left inguinal anatomy of a human patient are illustrated in order to particularly point out the usefulness of the present invention.

Generally, the inguinal hernia 45 is accessible through iliacus muscle 20. As can be well appreciated, an extremely sensitive network of vessels and nerves exist in the area of a typical inguinal hernia defect 45, which requires a surgeon to conduct a hernia repair with great skill and caution.

For instance, in the transverse abdominis aponeurosis 24, an internal ring 26 permits gastric vessels 30 and Vas deferens 33 to extend therethrough over an edge of inguinal ligament 28. Femoral canal 34 is located near Cooper's ligament 22 and contains external iliac vessels 36 and inferior epigastric vessels 38.

In many cases, the edge of the inguinal ligament 28 and Cooper's ligament 22 serve as anatomical landmarks and support structures for supporting surgical fasteners such as those mentioned previously. The area containing the external iliac vessels 36 and the Vas deferens 33 is commonly known to surgeons as "the Triangle of Doom". Accordingly, it is critical that the surgeon avoid injuring any of these vessels described above and extreme care must be taken when performing dissection, suturing or stapling within this area.

The Devices

The devices are used in a novel surgical procedure for the repair of a tissue defect 45, such as an inguinal hernia located within the inguinal floor. More specifically, the devices used in the novel surgical procedure are a prosthetic for the repair of tissue, and an energy based surgical device of the present invention for attaching the prosthetic to tissue by the application of pressure and energy.

Figure 1B:
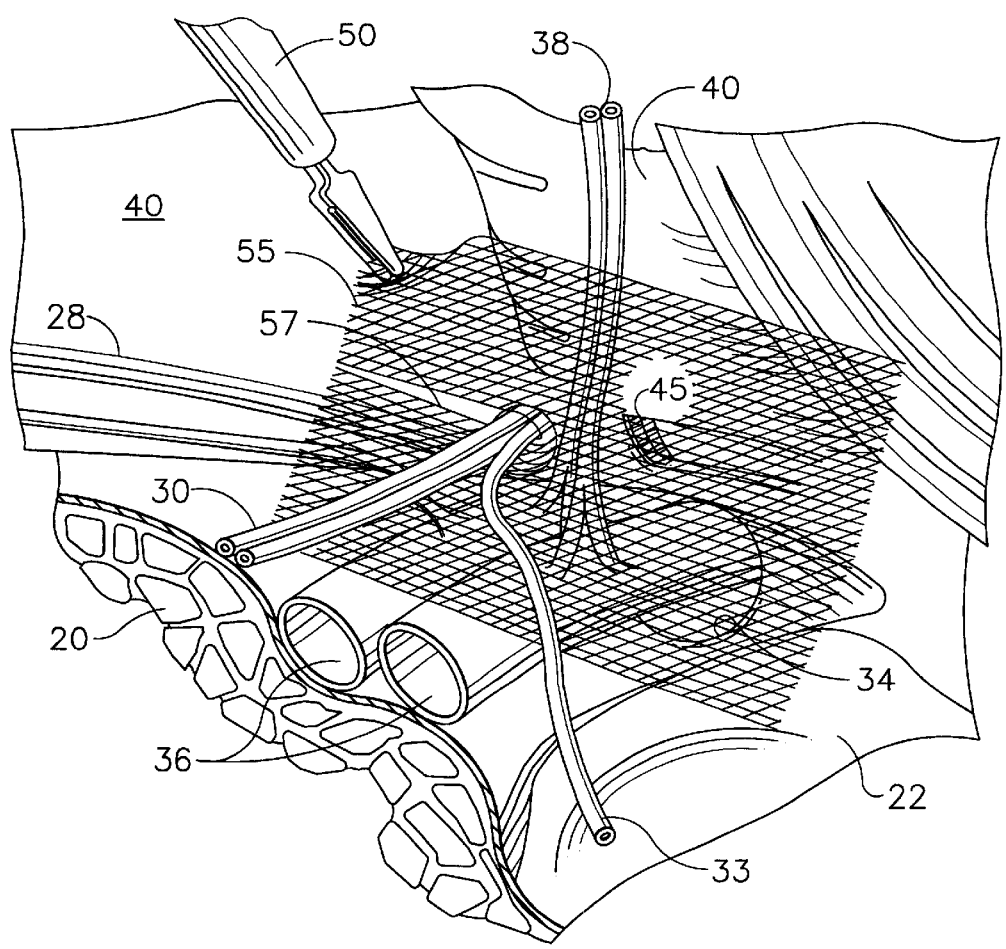
FIG. 1B is a fragmentary perspective view of a surgical instrument placing a mesh patch over the defect of FIG. 1A, according to the present invention.

FIG. 1B illustrates a prosthetic or mesh patch 55 for the repair of an inguinal hernia defect 45. The mesh patch 55 may consist of any desired configuration, structure or material. However, the patch 55 is preferably made of PROLENE™ (a known polymer made up of fibers) and preferably configured as mesh. It is within the training and comfort zone for surgeons to use the PROLENE™ mesh patch 55 since the patch 55 is easily sized, such as providing a side slot 57, for accommodating the gastric vessels 30 and the Vas deferens 33.

As illustrated, the patch 55 is placeable over the defect 45 for providing a sufficient barrier to internal viscera (not shown) of the abdomen which would otherwise have a tendency to protrude through the defect 45 and cause the patient a great deal of pain and discomfort.

The mesh patch 55 is attachable to the inguinal floor 40 by a novel two step method. A first application of pressure and energy is applied to the patch 55 by an energy based surgical device, henceforth referred to as energy device 100 (FIGS. 18A and 18B), to embed the patch 55 into the surrounding tissue. A second application of energy is applied to the same location to weld the tissue to the patch 55. The initial application of energy to the patch 55 and the surrounding tissue liquefies or emulsifies the surrounding tissue and the pressure pushes or embeds the mesh patch into the emulsified tissue. The second application of energy is of higher intensity than the first, and coagulates or tissue welds the emulsified tissue to the mesh patch and to the surrounding tissue. This forms a weld of sufficient strength to hold the patch 55 to the tissue surrounding the defect 45. The term "energy" refers to the application of Radio Frequency (RF) electricity, ultrasound (acoustic/mechanical) energy, or the combination thereof. The term "pressure" refers to the application of a force applied by any type of instrument or object to the patch 55 over the cross sectional area of the contact surface of these instruments or objects.

Accordingly, upon the dual application of energy and pressure to the patch 55 and the surrounding tissue, they adhere to each other thereby welding or anchoring the prosthetic patch 55 to the tissue. This makes choice of placement of the patch 55 easy, since it can be attached to most structures in the area of the defect 45. The operator is able to view through the mesh of the mesh patch 55 and can strategically place the welds without causing damage to delicate anatomical structures. In addition, the coagulated tissue will be replaced over time by human connective tissue.

Figure 18A:
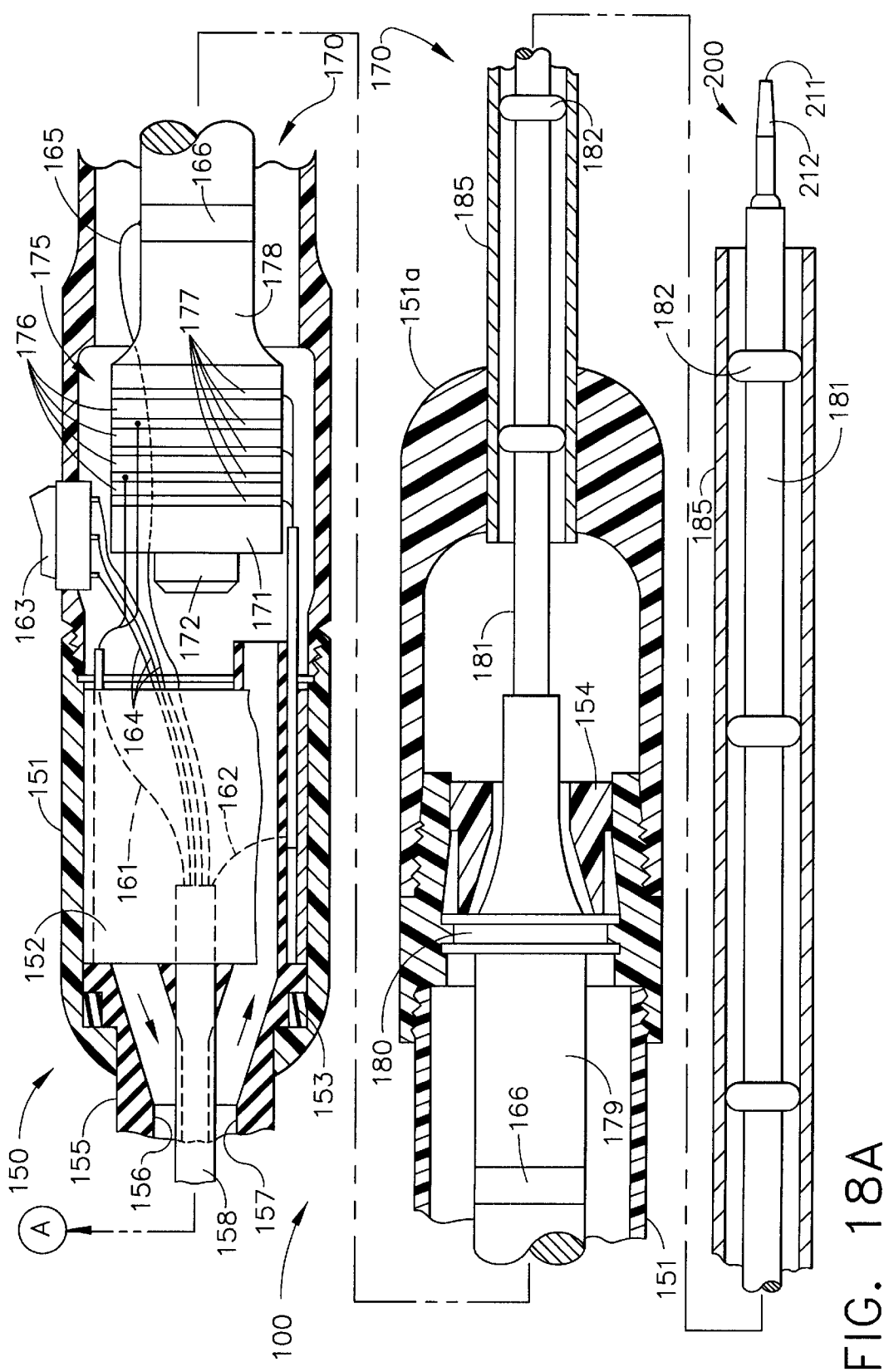
FIG. 18A is a cross sectional side view of a handpiece assembly according to the present invention.
Figure 18B:
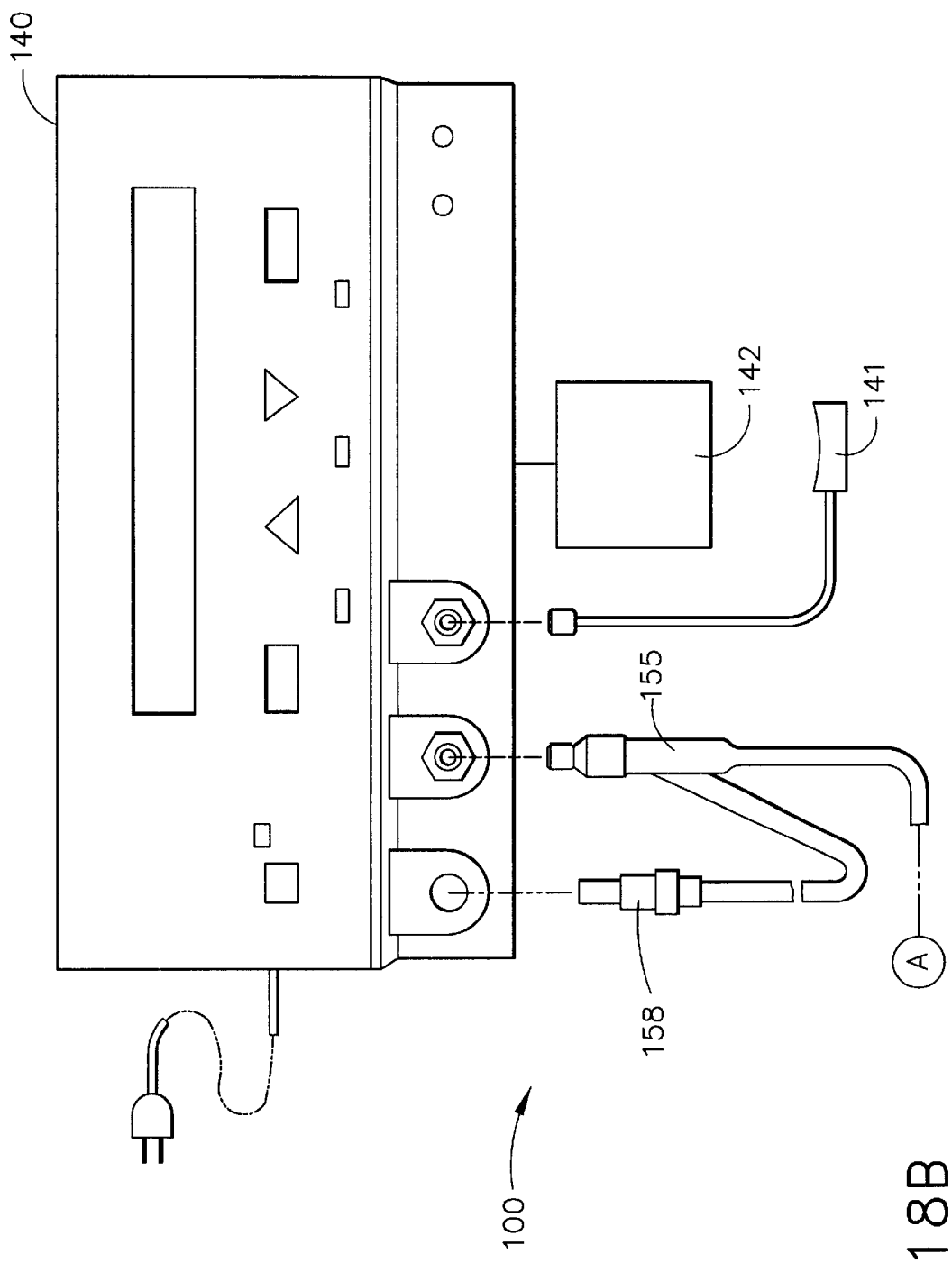
FIG. 18B is a front view of a generator assembly according to the present invention for the delivery of energy to the handpiece of FIG. 18A.

FIGS. 18A and 18B shows an embodiment of the energy based surgical device of the present invention for to securing the patch 55 to tissue with a dual application of pressure and energy. The energy device 100 of the present invention provides pressure and ultrasonic energy, and in some embodiments, Radio Frequency (RF) energy.

The energy device 100 of the present invention has a generator assembly 140 and a handpiece assembly 150. The handpiece assembly 150 has an acoustic assembly 170 for the generation of ultrasonic energy. The generator assembly 140 of the present invention generates both monopolar RF energy and an electrical signal that is converted to ultrasonic energy by the acoustic assembly 170. The electrical signal is produced at a selected amplitude, frequency, and phase determined by a control system of the generator assembly 140 and the electrical signal is transmitted from the generator to the acoustic assembly 170 by a power line 158. As will be described in greater detail later, the electrical signal is converted into mechanical motion (at a resonant frequency) by piezoelectric elements within the acoustic assembly 170. The acoustic assembly 170 is vibrated at a selected frequency and amplitude by high frequency longitudinal waves of ultrasonic energy resulting from the mechanical motion. The acoustic assembly 170 includes a waveguide 181 for transmission of the ultrasonic energy. A truncated cone end effector 200, located at the distal end of the waveguide 181 of the acoustic assembly 140, provides pressure and ultrasonic energy when placed into contact with tissue of the patient. The transfer of ultrasonic energy to tissue varies with the vibrational amplitude of the end effector 200, the amount of force applied by the user, the shape of the end effector, and the duration of the energy application. The transfer of RF energy to tissue generally varies with the contact force (to ensure adequate electrical connection), and the duration of the energy application.

The ultrasonic energy vibrates the distal end of the end effector 200 proximally and distally relative to the longitudinal axis of the handpiece assembly 150. The truncated cone end effector 200 has a distal, flat face embedding surface 211 perpendicular to the longitudinal axis and a coagulation surface 212 circumferentially located about the conical shape of the end effector 200 as best shown in FIGS. 14–17 and 18A. When the embedding surface 211 is brought into contact with tissue, the excursion or in and out motion of the embedding surface 211 of the end effector 200 causes mechanical tearing, cavitation, cell disruption, and emulsification of tissue. Thus, an application of ultrasonic energy from the embedding surface 211 will emulsify or liquefy tissue. The emulsified tissue is of a paste-like consistency and is formed from cells that have been exploded or emulsified by the creation of cavitation bubbles within the cellular structures. When the vibrating embedding surface 211 of the end effector 200 is used to push an object into contact with tissue, such as the mesh patch 55, the mesh vibrates along with the end effector 200 and effectively becomes an extension of the embedding surface 211 of the end effector 200. Thus, the vibrating mesh patch 55 emulsifies tissue directly beneath and adjacent to the mesh patch 55, and the application of pressure embeds the mesh patch 55 into the emulsified tissue.

A second effect is obtained when the coagulation surface 212 of the ultrasonic end effector 200 is brought into contact with tissue. The rapid excursion of the end effector 200 rubs the coagulation surface 212 of the blade back and forth against the tissue and generates friction or thermal energy within the cells. The thermal energy generated is sufficient to denature or coagulate tissue. Thus, when the coagulation surface 212 of the ultrasonic end effector 200 is applied to tissue such as emulsified tissue, the emulsified tissue is coagulated or tissue welded.

As illustrated in FIG. 18B, in one embodiment, the generator assembly 140 has a foot control 142 that is detachably coupled to the generator 140, preferably by a cable or cord, and in one embodiment is used to actuate the generator assembly 140 to provide energy to the handpiece assembly 150. A toggle switch 163 is located upon the handpiece 150 (FIG. 18A) and in a first embodiment is used to switch, but not activate, the generator from one type of energy production to the other, e.g. select RF energy, select ultrasound energy, or select a combination of RF and ultrasound energy. The toggle switch has a first position for ultrasonic energy, a second position for Radio Frequency energy and a third position for the combination of ultrasonic energy and Radio Frequency energy. In an alternate embodiment, the toggle switch 163 can be used to select the energy type and activate the generator assembly 140, thus bypassing the foot control 142.

When actuated, the generator assembly 140 supplies electrical energy to the acoustic assembly 170 in the form of electrical signals. The generator assembly 140 has a phase lock loop control system to adjust the frequency of the electrical signals to match the resonant frequency of the acoustic assembly 170. The generator assembly 140 also has a second feedback loop to maintain a constant electrical current level in order to maintain a constant vibrational amplitude, or excursion, at the distal end of the end effector 200. Thus, this second feedback loop maintains constant excursion when the end effector is subjected to tissue contact or load. The electrical signal supplied to the acoustic assembly 170 vibrates the end effector 200 at a frequency range preferably between 20 kHz to 250 kHz, and more preferably between 54 kHz to 56 kHz.

A pad 141 connects to the right most connector of the generator assembly 140 and provides the return ground path for the application of monopolar RF energy. The pad 141 is placed under the patient to provide a return ground and can be coated with a conductive paste or gel to enhance the electrical connection with the patient. A positive RF lead 165 (FIG. 18A) operably connects the generator assembly 140 to the acoustic assembly 170 and to the end effector 200 through the waveguide 181 which is made of an electrically conductive material. When the end effector 200 is placed into contact with the patient, and the generator assembly 140 is activated, the RF circuit is complete and RF energy is applied to the patient. The RF lead 165 is one lead of many located within the power line 158. The power line 158 connects to the left most connector of the generator assembly 140 and enters an air line 155. The air line 155 attaches to the distal end of the handpiece assembly 150 and is formed from a flexible engineering plastic with multiple passageways within, and for this particular embodiment, is formed from a silicone extrusion. One passageway within the air line 155 carries the power line 158 to the handpiece assembly 150. Two additional passageways within the air line 155 provide a conduit for passage of air from a cooling pump within the generator assembly 140 to cool the handpiece assembly 150, and an air conduit back to the generator for venting warm cooling air to the atmosphere.

As illustrated in the sectioned handpiece assembly 150 of FIG. 18A, the air line 155 is attached to the proximal end of housing 151 of the handpiece assembly 150. A supply air passageway 157 and a return air passageway 156 are located in the handpiece assembly 150 for cooling purposes. The power line 158 is centered within the air line 155 and a number of electrical wires or leads extend to the right from the power line. As shown, the distal ends of a number of switch leads 164 are connected to the toggle switch 163. The proximal ends of these switch leads 164 connect to the generator assembly 140 and carry the signal to switch the generator assembly 140 from one type of energy production to the other. A positive lead 161 and a ground lead 162 extend from the power line 158 and are electrically coupled to a transducer stack 175 of the acoustic assembly 170. The positive lead 161 and ground lead 162 carry the electrical signals from the generator assembly 140 to the transducer stack 175 where they are converted to mechanical motion (at a resonant frequency) and ultrasonic energy. A RF lead 165 is electrically connected to the acoustic assembly 170 by a conductive element 166 for the conduction of RF energy from the generator, to the acoustic assembly, and to the end effector 200. The leads are surrounded by a non-conducting insulator ring 152.

The acoustic assembly 170 generally includes the transducer stack 175 for the generation of ultrasonic energy, a front bell 178 and a front mount 179 for transmission of ultrasonic energy from the transducer stack 175. The waveguide 181 is operatively coupled to the front mount 179 for the transmission of ultrasonic energy to the end effector 200 for the transmission of ultrasonic energy to the tissue. The front mount 179 also has a resilient mounting ring 180, preferably silicone, to suspend and vibrationally isolate the acoustic assembly 170 from the handpiece assembly 150. The acoustic assembly 170 operates at a preset vibrational frequency as stated above, and to accomplish this, it is preferable to acoustically tune the length of each element above to an integral number of ½ of the preselected system wavelength of the vibrational frequency. With the exception of the transducer stack 175, the elements of the acoustic assembly 170 are generally formed from a solid core material that propagates ultrasonic energy such as titanium alloy (i.e. Ti-6Al-4V) or an aluminum alloy. It is of note that the materials used for the elements (other than the transducer stack 175) of the acoustic assembly 170 are electrically conductive.

The transducer assembly 175 of the acoustic assembly 170 converts the electrical signals from the generator assembly 140 into mechanical motion and ultrasonic energy. As shown in FIG. 18A, the transducer assembly 175, also known as a "Langevin stack" is formed from an alternating stack or sandwich of electrically conductive contact washers 177 and annular piezoelectric elements 176 therebetween. The contact washers 177 are alternately electrically coupled to the positive lead 161 and to the ground lead 162 extending from the power cable 158, e.g. each contact washer 177 preceding and following a selected contact washer 177 is of the opposite electrical pole. The piezoelectric effect is well known in physics and is a characteristic of certain types of materials to either change shape upon an application of electrical energy, or to generate electrical energy when compressed. The piezoelectric elements 176 may be fabricated from any suitable material exhibiting the "piezoelectric effect" such a s lead zirconate, lead titanate, or ceramic crystal material. The piezoelectric elements 176 are held operably coupled in compression between a proximal end bell 171 and a distal front bell 178, by a preload bolt 172. The application of electrical signals from the generator assembly 140 to the piezoelectric elements 176 forces the piezoelectric elements 176 to undergo a rapid series of physical expansions and contractions. These rapid expansions and contractions send a series of mechanical pulses or high frequency longitudinal waves of ultrasound energy down the acoustic assembly 170 to the end effector 200. The operation of a transducer stack 175 generates heat and can require cooling, such as that provided by air from the supply air passage 157.

The distal front bell 178 is operatively coupled to the front mount 179 by an internal threaded connection, and has the conductive element 166 of the present invention compressed therebetween. The conductive element 166 is washer shaped with a clearance hole for passage of the threaded connection therein, and formed from an electrically and a vibrationally conductive material such as a titanium alloy or an aluminum alloy. The conductive element 166 is an active element of the acoustic assembly 170 and is the conduit for the conduction of RF electrical energy from the generator assembly 140 to the electrically conductive elements of the acoustic assembly 170. Whereas the RF energy conductive element 166 is a washer, it is also conceivable to one skilled in the art that there are a number of different methods of attaching the RF lead 166 to the acoustic assembly 170.

The acoustic assembly 170 is resiliently suspended and constrained within the handpiece assembly 150 by the mounting ring 180, which is captured between the housing 151 and a retainer 154. The front mount 179 and mounting ring 180 generally constrain the acoustic assembly 170 from axial and rotational motion within the housing 150. The housing 150 is a hollow elongated shell formed from an engineering plastic or thermoplastic of sufficient rigidity and strength, such as polycarbonate, polyamid and the like. The housing 150 can be formed from a single piece or multiple elements and still serve the intended function. The housing 150 is open at the proximal end for the reception of the air line 155 and a seal 153 therein. The toggle switch 163 extends through the upper portion of the housing 150. At the distal end, a front housing 151a is threadedly connected to the housing 151. An attached tube 185 extends distally from the front housing 151a. The front housing 151a is removable to expose the distal end of the front mount and the waveguide 181.

The waveguide 181 is a solid core ultrasonic transmission element of the acoustic assembly, having a threaded connector (not shown) on the proximal end and an end effector 200 extending from the distal end. The waveguide 181 is constructed from an electrically and vibrationally conductive material such as an aluminum alloy or a titanium alloy. A number of resilient annular isolation bushings 182 are spaced at nodes longitudinally down the waveguide 181 to vibrationally isolate the waveguide 181 from contact with the tube 185 of the front housing 151a. The waveguide 181 is constructed in this manner so as to permit rapid interchange of the waveguide 181 (and the attached end effector 200) with the acoustic assembly 170. Thus, the operator can place a different end effector upon the energy device 100 by simply removing the front housing 151a, removing the installed waveguide 181 from the handpiece assembly 150, installing a new waveguide with a different end effector, and reinstalling the front housing 151a.

Figure 6:
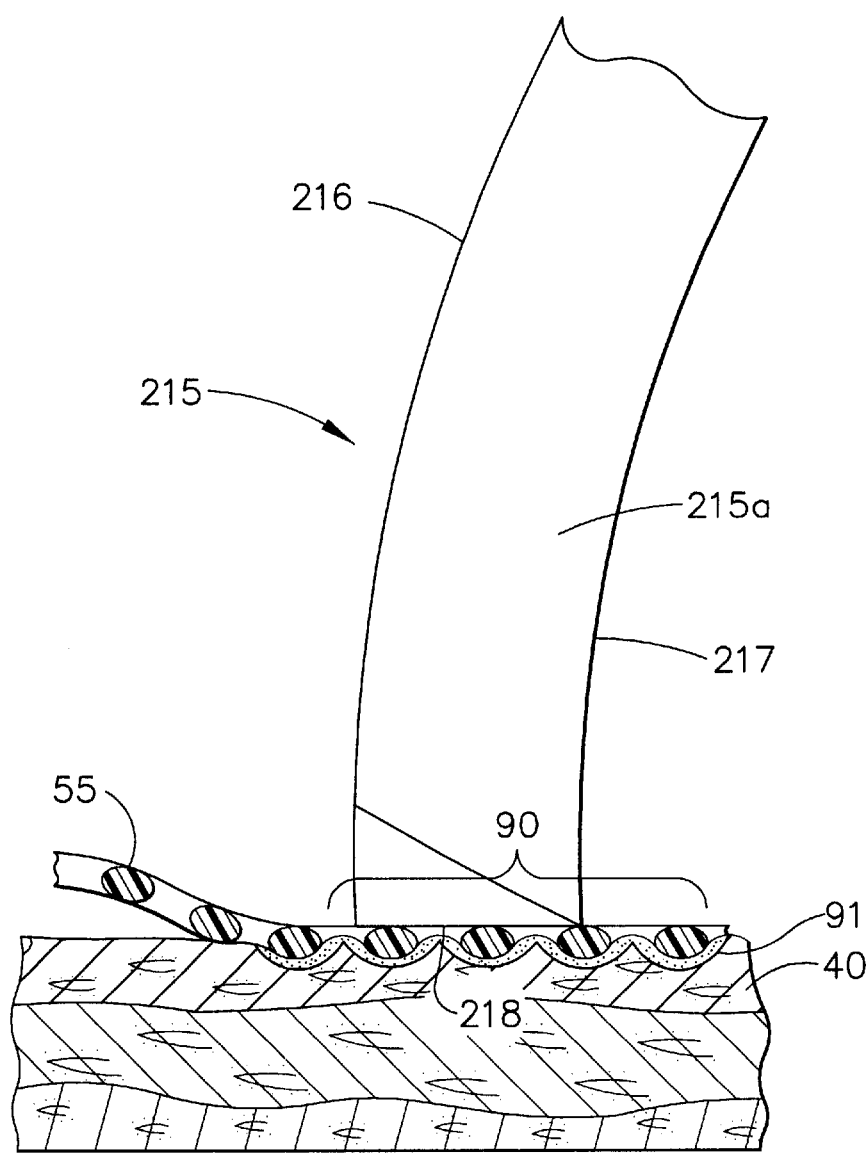
FIG. 6 is a cross sectional side view of the inguinal floor and the mesh patch of FIG. 2 illustrating the method, according to the present invention, of embedding of the mesh patch to the inguinal floor with the curved end effector.
Figure 7:
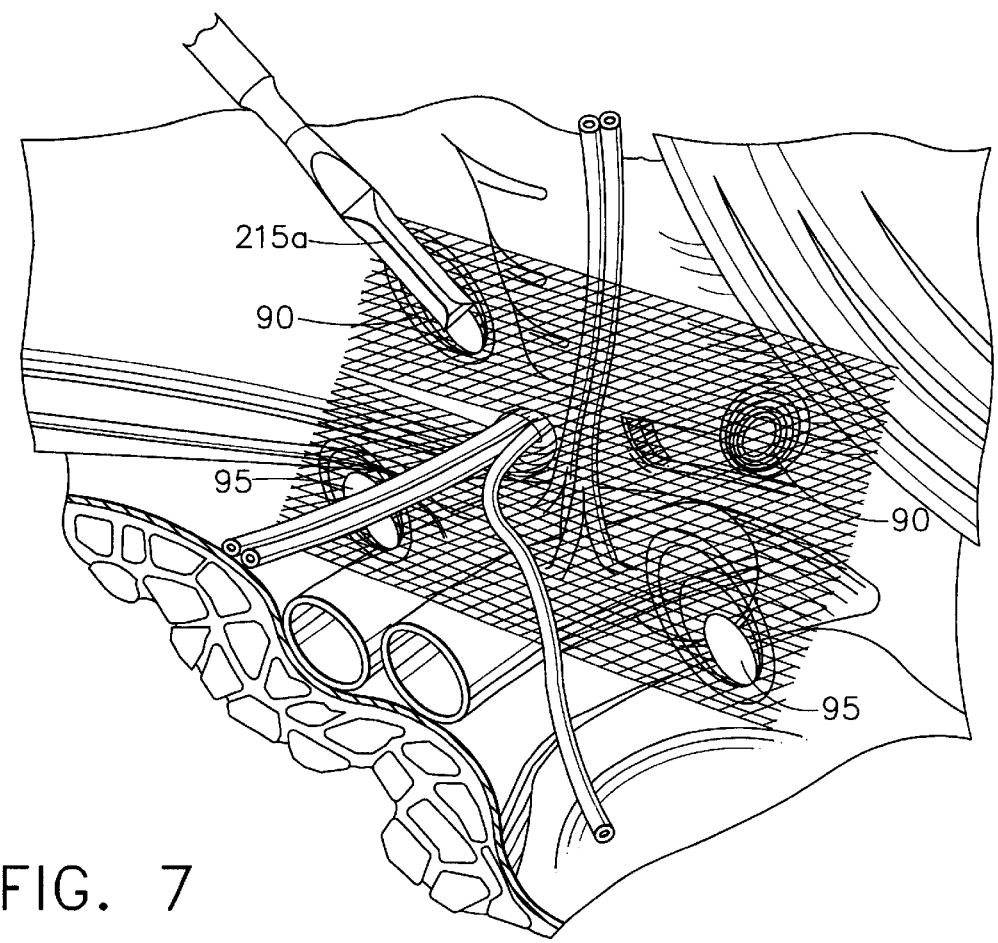
FIG. 7 is a fragmentary perspective view of welding the mesh patch to the inguinal floor by coagulating an embedded area of FIG. 6 with the curved end effector of FIG. 3 according to the present invention.
Figure 8:
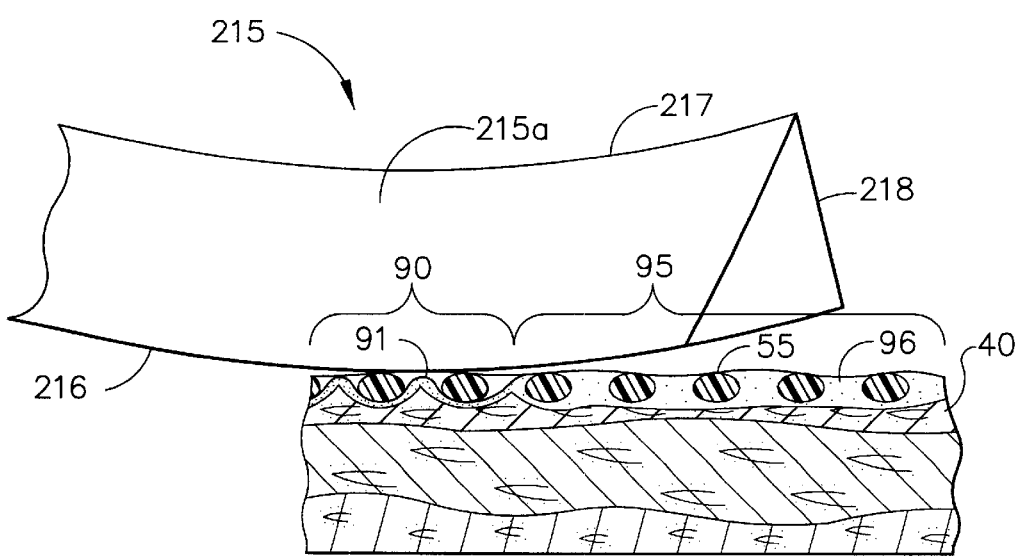
FIG. 8 is a cross sectional side view of a partially coagulated area of FIG. 7 showing the welding of the mesh patch to the inguinal floor with the curved end effector of FIG. 3 of the present invention.

A second embodiment of an end effector for the attachment of the patch 55 to tissue is shown in FIGS. 3–8. A curved end effector 215 is shown having a curved member 215a that includes a curved outer surface 216, a curved inner surface 217 and a tip surface 218. The tip surface 218 is used as an embedding surface and the curved outer surface 216 is used as a coagulating surface in a manner similar to the use of the end effector 200 described above. The end effector 215 can be used to provide ultrasonic energy or RF energy to tissue. As described above, the embedding surface 218, when used with ultrasonic energy causes mechanical tearing, cavitation and cell disruption, and emulsification of tissue (FIGS. 5–6). When the coagulating surface 216 is used with ultrasonic or RF energy, it causes coagulation and dessication of tissue. The coagulating surface 216 of the end effector 215 is especially adapted for the coagulation and desiccation of tissue. When used with ultrasound energy, the outer curved surface 216 applies thermal energy that coagulates tissue. The curved shape of the curved member 215a enables a large area of the outer curved surface 216 to come into contact with tissue, thus decreasing the time required to coagulate a large area of tissue (FIGS. 7–8). Likewise, when the outer curved surface 216 is used with RF energy, the same large contact area is available.

Figure 9:
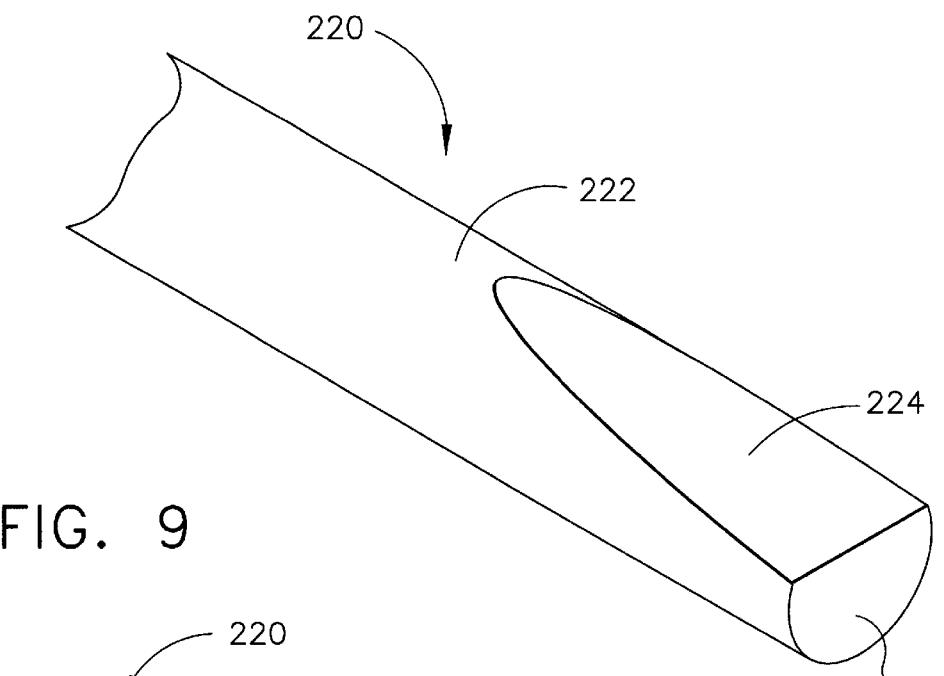
FIG. 9 is a fragmentary perspective view of an angled surface end effector of the present invention.
Figure 10:
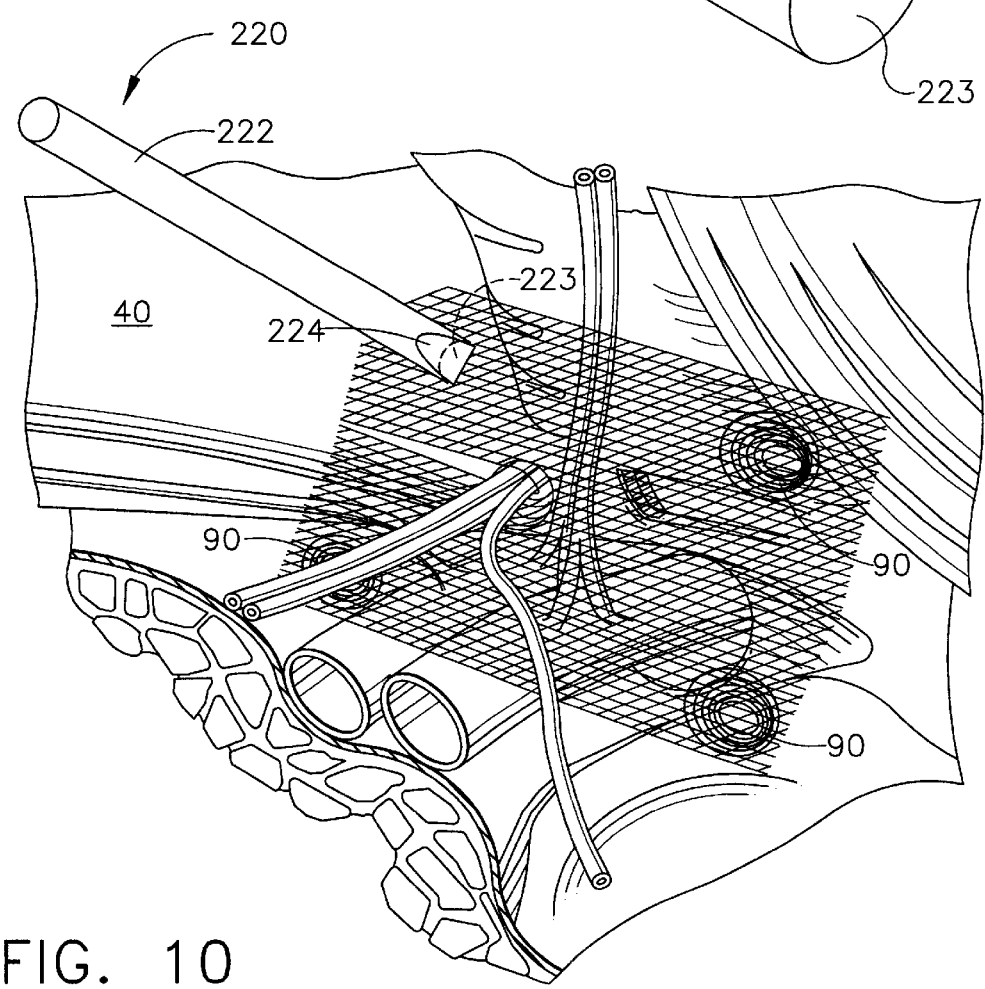
FIG. 10 is a fragmentary perspective view of the end effector of FIG. 9, performing the step of embedding the prosthetic into the inguinal floor according to the present invention.
Figure 11:
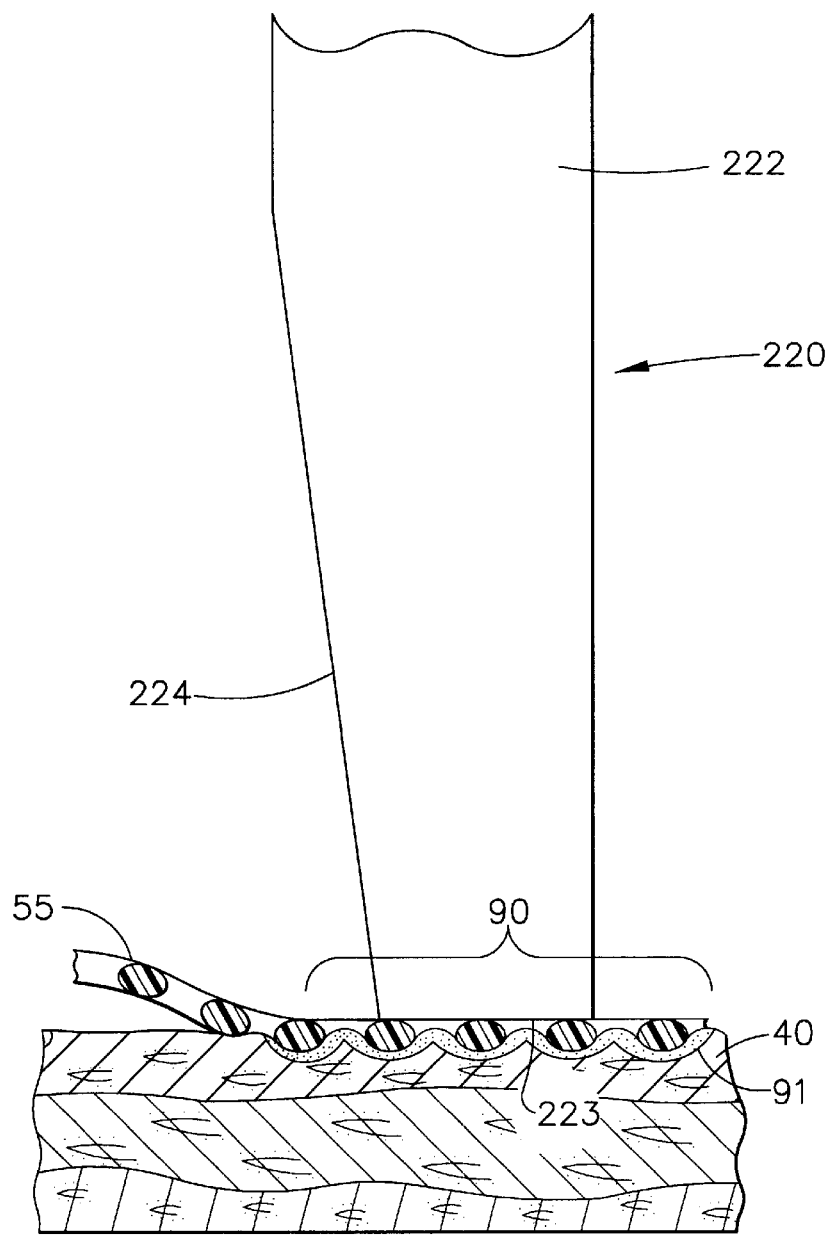
FIG. 11 is a cross sectional side view of the inguinal floor and the mesh patch of FIG. 10 showing the embedding of the mesh patch to the inguinal floor with the end effector of FIG. 9.

A third embodiment of an end effector for the attachment of the mesh patch 55 to surrounding tissue is shown in FIGS. 9–13. The novel end effector is an angled surface end effector 220 having a cylindrical shaft 222 and a generally circular distal face or embedding surface 223 perpendicular to the longitudinal axis of the cylindrical shaft 222. An angled beveled surface or coagulation surface 224 extends proximally from the embedding surface 223 (FIG. 9). The beveled surface 224 is a coagulation surface which is angled from the longitudinal axis of the angled surface end effector 220 and angles outwardly from the distal face 223, e.g. the embedding surface in the proximal direction. Like the tip 218 of the curved end effector 215, the embedding surface 223 of the angled surface end effector 220 is especially adapted for emulsification of tissue (FIGS. 10–11). The angled coagulation surface 224 provides a broad flat area of tissue contact, and enables the handpiece assembly 150 to be angled to the tissue surface (FIGS. 12–13) at the end effector 220 for performing the welding step such as described above.

The Method

Although the present invention is applicable to various surgical procedures involving the curing or repairing of tissue defects, three methods using different end effectors according to the present invention are illustrated in FIG. 1, FIGS. 4–8, and FIGS. 10–17 in accordance with the repair of an inguinal hernia 45 located in the left inguinal region of a human patient.

Figure 2:
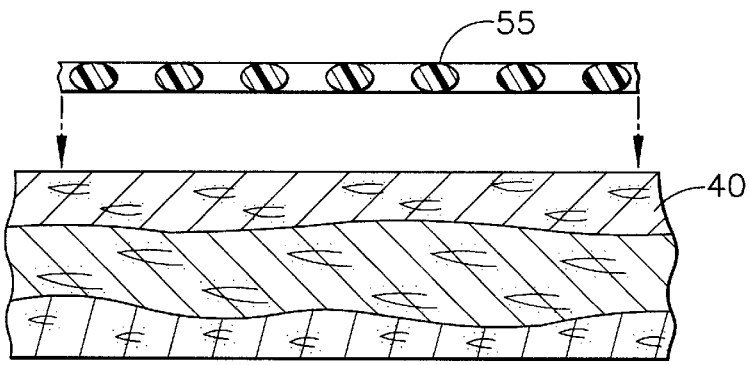
FIG. 2 is a cross sectional side view of the inguinal floor of the lower abdomen of FIG. 1B illustrating the placement of the mesh patch above the tissue in preparation for repair of the defect, according to the present invention.

As best shown in FIGS. 1A, 1B and 2, in repairing a tissue defect 45, the surgeon accesses the defect 45 with caution and carefully identifies the anatomical structures and landmarks as well as the tissue surrounding the defect 45 such as the inguinal floor 40, aponeurosis 24, Cooper's ligament 22, etc. Additionally, if any internal viscera had extended through the defect 45, the surgeon gently moves the viscera back through the defect 45 and into the abdominal cavity. The surgeon then determines the location for placement of the prosthetic or mesh patch 55 on the tissue surrounding the defect 45. The patch 55, which may be standard PROLENE™ mesh, is sized and configured for a customized fit at the site. Next, as shown in FIG. 1B, the patch 55 is placed on the tissue around the defect 45 using an instrument 50 such as standard forceps or laparoscopic graspers, if the repair is being conducted with the aid of an endoscope as part of laparoscopic procedure (FIGS. 1B and 2). The side slot 57 is used to accommodate vessel structures 30 and 33 in a safe and convenient manner. Accordingly, the gastric vessels 30 and the Vas deferens 33 are positioned in the side slot 57 and surrounded by the remainder of the mesh patch 55.

Once the patch 55 is placed over the defect 45, the surgeon applies a first application of pressure and energy to the patch 55 and to the surrounding tissue or inguinal floor 40 to embed the mesh patch 55 through the use of the device 100. The first application of pressure and energy, preferably ultrasonic energy, is applied by the embedding surface 211, 218 and 223 of the end effector 200, 215 and 220 respectively and emulsifies or liquefies the tissue or inguinal floor directly beneath the mesh of the patch 55. The pressure from the embedding surface 211, 218 and 223 of the end effector 200, 215 and 220 respectively embeds the patch 55 into the emulsified tissue. A second application of energy is applied by the surgeon at the coagulation surface 212, 216 and 224 of the end effector 200, 215 and 220 respectively to coagulate the emulsified tissue around the embedded patch 55 and weld the patch 55 to surrounding tissue. If the surgeon is using the same type of energy for the first application as for the second application, the energy intensity requirements are different. It is desirable that the second application of energy is applied at a greater energy intensity than the first energy application to ensure coagulation. Pressure is not as critical during the second application of energy except as a means to ensure energy transfer to the emulsified tissue. With multiple applications of pressure and energy to preferred mesh attachment positions upon the patch 55 and the surrounding tissue, patch 55 is securely anchored over the defect 45. Accordingly, a sufficient barrier is provided to the defect 45 and internal viscera are prevented from entering through the defect 45.

FIGS. 3–8 illustrate a method of use of the second embodiment of the ultrasonic curved end effector 215. As best shown in FIG. 5, the surgeon uses the tip or embedding surface 218 of the curved member 215a to push the patch 55 against the inguinal floor 40 just prior to the application of ultrasonic energy. The surgeon applies pressure and ultrasonic energy to three other preferred attachment positions as well. The applications of pressure and energy emulsify the tissue beneath the attachment positions and the patch 55 is pushed into emulsified tissue 91, thus creating embedded areas 90 as shown. FIG. 6 is a side view of an embedded area 90 and the curved member 215a of the end effector 215 showing the end effector 215 emulsifying the tissue of the inguinal floor 40 beneath the patch 55 at the embedding surface 218. The patch 55 is embedded into the emulsified tissue 91 by embedding surface 218. As shown in FIG. 7, the surgeon applies the second application of energy and pressure to weld the mesh patch 55 to the inguinal floor 40. Coagulated areas 95 are created with the end effector 215 in the process of welding the patch 55 to the inguinal floor 40. This welding is accomplished by utilizing the coagulation surface 216 of the curved end effector 215 in contact with the emulsified tissue 91 of the upper left embedded area 90, by applying energy to coagulate or to weld the mesh patch 55 to the inguinal floor 40 at the outer surface 216. The pressure needed for the second application of energy is light and is needed to merely maintain contact between the end effector 215 and the tissue for the transfer of energy. This second application of energy can be ultrasound energy, RF energy or a combination of RF and ultrasound energy. FIG. 8 is a side view of the curved end effector 215 and the third coagulated area 95 wherein the surgeon uses the coagulation surface 216 to create a coagulated area 95 from an embedded area 90.

Figure 12:
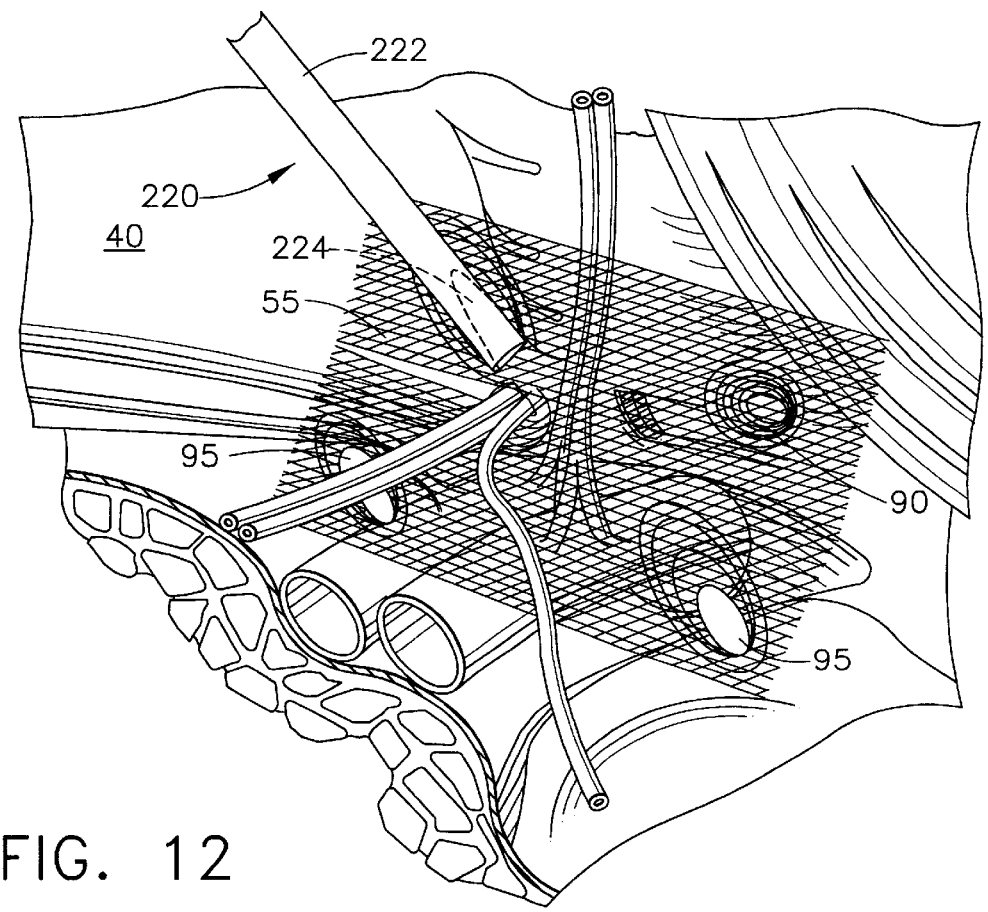
FIG. 12 is a fragmentary perspective view of the end effector of FIG. 9 illustrating the welding of the mesh patch to the inguinal floor according to the present invention.
Figure 13:
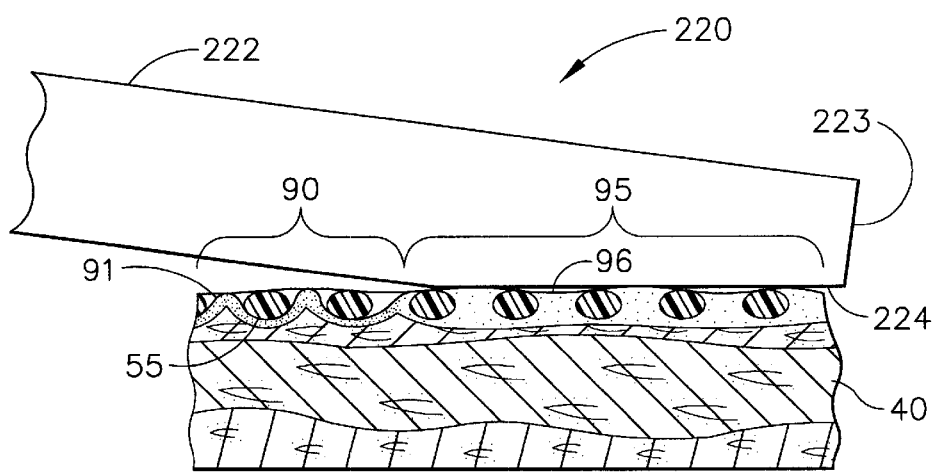
FIG. 13 is a cross sectional side view of the partially coagulated area of FIG. 12 showing the welding of the mesh patch to the inguinal floor with the end effector of FIG. 9.

FIGS. 9–13 shows the method of use of the third embodiment of the end effector, angled surface end effector 220 (FIG. 9). As shown in FIG. 10, the surgeon uses the embedding surface 223 of the angled surface end effector 220 to push the patch 55 into the inguinal floor 40 prior to the application of ultrasonic energy. The surgeon applies the first application of pressure and ultrasonic energy to create embedded areas 90. FIG. 11 shows a side view of the embedding of the patch into the emulsified tissue 91 of the inguinal floor 40 by the application of ultrasonic energy to the mesh patch 55 and to the inguinal floor 40 at the embedding surface 223. In FIG. 12, the surgeon creates coagulated areas 95 or welds by applying energy from the angled coagulation surface 224 of the angled surface end effector 220 in order to create welds 95. As stated above, this second step can be performed using RF energy, ultrasound energy, or a combination of RF and ultrasound energy. FIG. 13 is a side view showing the coagulation of emulsified tissue using the angled surface 224.

Figure 14:
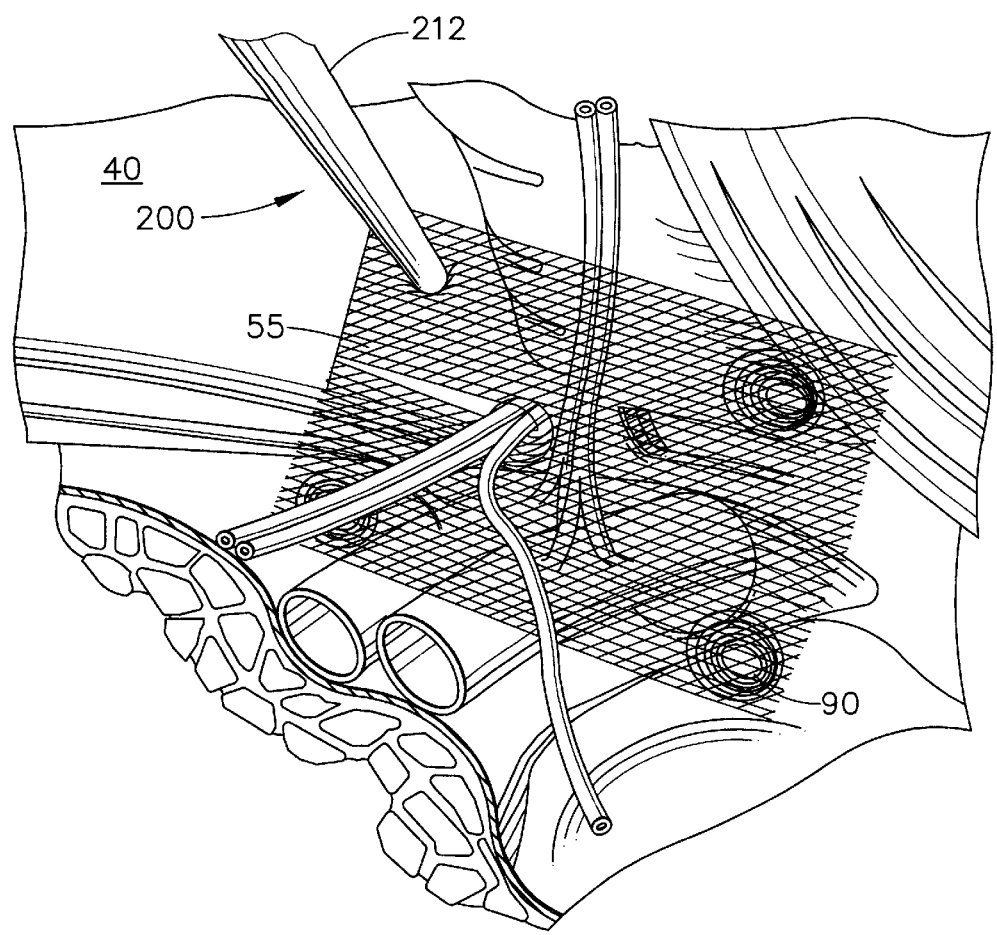
FIG. 14 is a fragmentary perspective view of a truncated cone end effector of the present invention applying an initial application of energy to embed the prosthetic into surrounding tissue.
Figure 15:
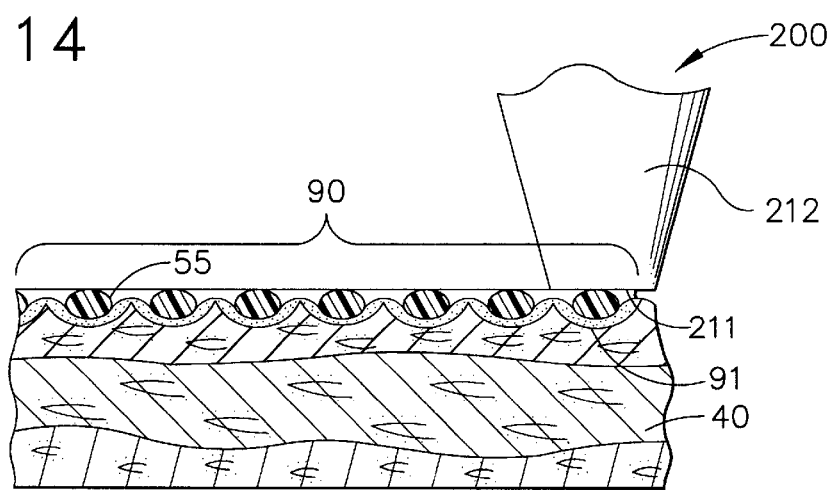
FIG. 15 is a cross sectional side view of the inguinal floor and the mesh patch of FIG. 14 illustrating the embedding of the mesh patch to the inguinal floor with the end effector of FIG. 14 according to the present invention.
Figure 16:
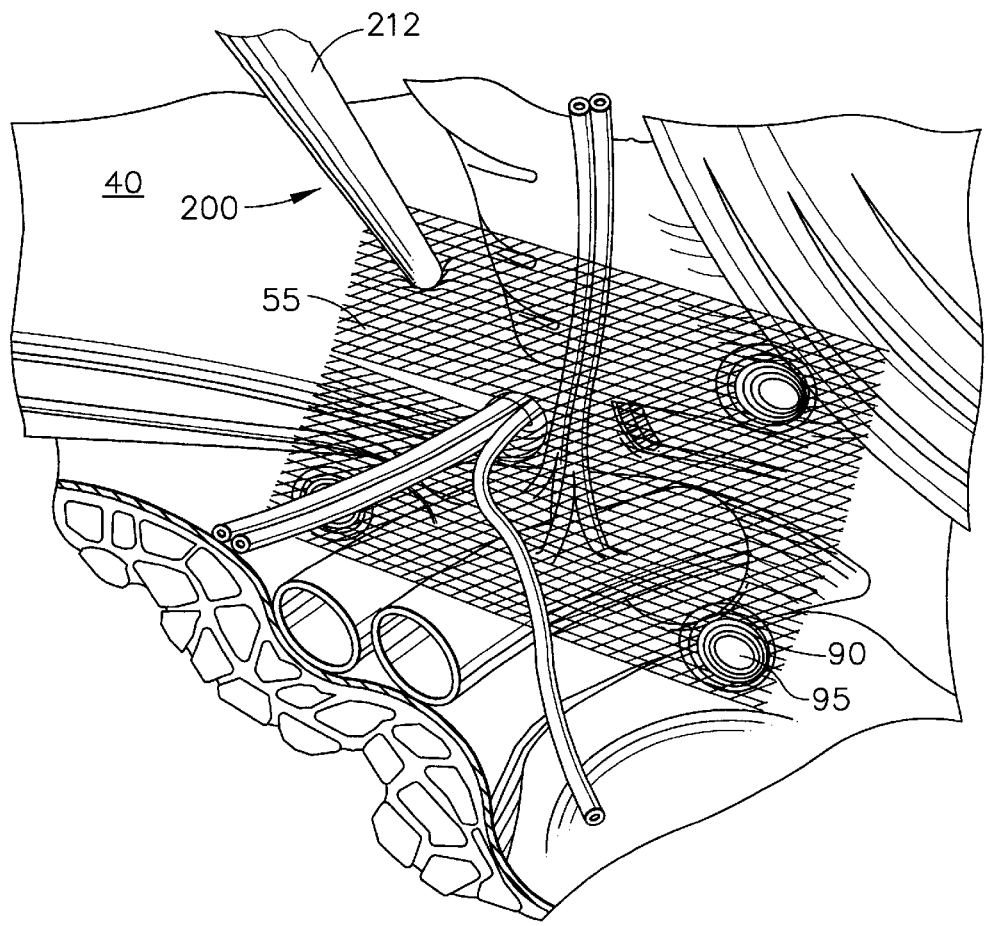
FIG. 16 is a fragmentary perspective view of FIG. 14 showing the prosthetic welded to tissue at three welded areas wherein the end effector of FIG. 14 is shown applying a first application of energy to embed the prosthetic at a fourth site according to the present invention.
Figure 17:
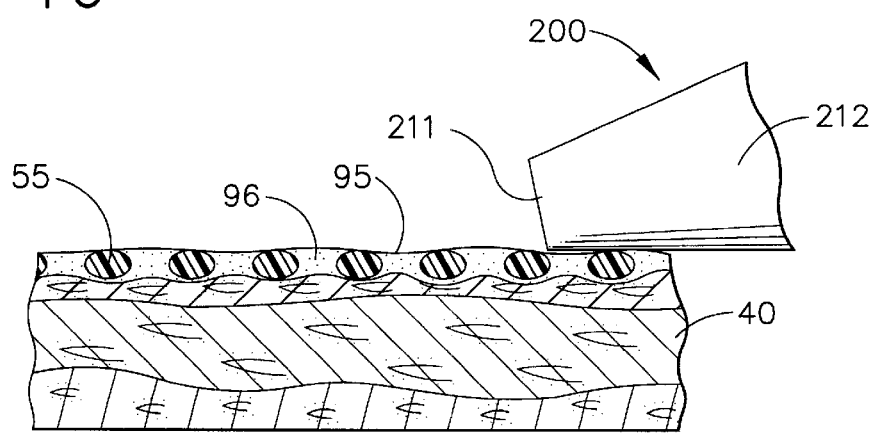
FIG. 17 is a cross sectional side view of a partially coagulated area of the inguinal floor showing the end effector of FIG. 14 welding the mesh patch to the surrounding tissue according to the present invention.

The truncated cone end effector 225, and the method of use are shown in FIGS. 14–17. As shown in FIG. 14, the surgeon uses embedding surface 211 to push the mesh 55 into the inguinal floor 40 just prior to the application of energy to emulsify the underlying tissue. The surgeon creates embedded areas 90 through this step. FIG. 15 shows the results of the initial application of energy and pressure to an embedded area wherein the mesh patch 55 is embedded into the inguinal floor 40. As shown in FIG. 16, the surgeon coagulates the tissue at the embedded areas 90 (FIG. 14). The truncated cone end effector 225 is used to push the mesh patch 55 into the inguinal floor with the embedding surface 211, just prior to the first application of energy. After the initial application of energy to embed the mesh patch 55, the surgeon will tip or rotate the truncated cone end effector about the distal end to bring the circumferential coagulating surface 212 into contact with the emulsified tissue 91 for the second application of energy in a manner similar to the methods described for end effectors 215 and 220. FIG. 17 is a side view of the coagulated tissue 96 within one of the coagulated areas 95 showing the patch 55 welded onto the inguinal floor 40. As with the two previous end effectors, the second application of energy can be ultrasonic energy, RF energy, or a combination of RF and ultrasonic energy.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method for repairing a defect in tissue comprising the steps of:
    a) placing a prosthetic over a tissue defect and against surrounding tissue;
    b) embedding a prosthetic into surrounding tissue by a first application of pressure and ultrasonic energy to said prosthetic and said surrounding tissue on at least one location on said prosthetic and said surrounding tissue; and
    c) welding said embedded prosthetic into said surrounding tissue by an application of pressure and Radio Frequency energy on said at least one location.

2. The method of claim 1 including applying said first application of pressure and ultrasonic energy to said prosthetic and said surrounding tissue at a plurality of locations on said prosthetic and said surrounding tissue.

3. The method of claim 2 including applying Radio Frequency energy to said prosthetic and said surrounding tissue at said plurality of locations.

4. The method of claim 3 wherein said ultrasonic energy is applied at a frequency between 20 kHz to 250 kHz.

5. The method of claim 4 wherein said ultrasonic energy is applied at a frequency between 54 kHz and 56 kHz.

6. The method according to claim 1 wherein said application of pressure and ultrasonic energy to said prosthetic and said surrounding tissue emulsifies said surrounding tissue and embeds said prosthetic into emulsified surrounding tissue.

7. The method according to claim 6 wherein said application of pressure and Radio Frequency energy to said embedded prosthetic and said emulsified surrounding tissue converts said emulsified surrounding tissue into coagulated surrounding tissue and welds said coagulated surrounding tissue around said embedded prosthetic and to said surrounding tissue.

8. The method of claim 7 including applying said pressure and ultrasonic energy to said prosthetic and said surrounding tissue at a plurality of locations on said prosthetic and said surrounding tissue.

9. The method of claim 8 including applying pressure and Radio Frequency energy to said prosthetic and said surrounding tissue at said plurality of locations.

10. The method of claim 9 wherein said ultrasonic energy is applied at a frequency between 20 kHz to 250 kHz.

11. The method of claim 10 wherein said ultrasonic energy is applied at a frequency between 54 kHz and 56 kHz.

* * * * *